United States Patent [19]
Mutoh et al.

[11] Patent Number: 5,496,850
[45] Date of Patent: Mar. 5, 1996

[54] ANTIMETASTASIS AGENT OF MALIGNANT TUMORS

[75] Inventors: Masato Mutoh, Yokohama; Masakazu Hattori, Nagaokakyo; Shintaro Nishio, Ebina; Kiyotaka Ohno, Fujisawa, all of Japan

[73] Assignee: Toray Industries, Inc., Tokyo, Japan

[21] Appl. No.: 244,668

[22] PCT Filed: Oct. 9, 1992

[86] PCT No.: PCT/JP92/01313

§ 371 Date: Aug. 8, 1994

§ 102(e) Date: Aug. 8, 1994

[87] PCT Pub. No.: WO94/08584

PCT Pub. Date: Apr. 28, 1994

[30] Foreign Application Priority Data

Apr. 11, 1991 [JP] Japan ................................. 3-78819

[51] Int. Cl.⁶ .................................................. A61K 31/34
[52] U.S. Cl. ............................................................ 514/468
[58] Field of Search .............................................. 514/468

[56] References Cited

FOREIGN PATENT DOCUMENTS

| | | |
|---|---|---|
| 0421562 | 4/1991 | European Pat. Off. . |
| 57-144276 | 9/1982 | Japan . |
| 58-124778 | 7/1983 | Japan . |
| 92/14438 | 9/1992 | WIPO . |

OTHER PUBLICATIONS

Chemical Abstracts, vol. 118, No. 13, 29 Mar. 1993 abstract No. 116744e.
Dialog Information Services, File 155: Medline, accession No. 07133831' Abstract Aug. 1989.
Drugs of the Future, vol. 18. No. 1, 1993 pp. 29–48, Schneider et al.

*Primary Examiner*—Jerome D. Goldberg
*Attorney, Agent, or Firm*—Birch, Stewart, Kolasch & Birch

[57] ABSTRACT

An agent which is chemically stable, which prominently inhibits metastasis of malignant tumor and which is safe is disclosed. The antimetastasis agent of malignant tumors according to the present invention comprises as an effective ingredient beraprost or a pharmaceutically acceptable salt thereof.

2 Claims, No Drawings

ANTIMETASTASIS AGENT OF MALIGNANT TUMORS

This application is a 371 of PCT/JP92/01313 filed Oct. 9, 1992.

TECHNICAL FIELD

This invention relates to an antimetastasis agent of malignant tumors.

BACKGROUND ART

Metastasis of malignant tumors is positioned as the terminal phase in the process of progress of tumors, which is a malignant phenotype that leads the patients to death. At present, chemotherapy agents are mainly used for inhibiting metastasis accompanied by enucleation of tumors. However, satisfactory results are not always obtained. Thus, development of an antimetastasis agent having high effectiveness is desired.

Recently, it was reported that prostaglandin $I_2$ ($PGI_2$) and the like are effective against hematogenous metastasis of mouse tumors (see Science, Vol. 212, 1270, (1981)). However, these compounds are unstable so that they cannot be systemically administered as pharmaceuticals.

DISCLOSURE OF THE INVENTION

Accordingly, an object of the present invention is to provide an antimetastasis agent of malignant tumors, which effectively inhibits metastasis of malignant tumors and which is safe.

That is, the present invention provides an antimetastasis agent of malignant tumors comprising as an effective ingredient beraprost or a pharmaceutically acceptable salt thereof.

The antimetastasis agent according to the present invention prominently inhibits the metastasis of malignant tumors and is safe. Further, it is chemically stable.

BEST MODE FOR CARRYING OUT THE INVENTION

The compound name of beraprost which is used as an antimetastasis agent of malignant tumors according to the present invention is (±)-(1R*,2R*,3aS*,8bS*)-2,3,3a,8b-tetrahydro-2-hydroxy-1-[(E)-(3S*)-3-hydroxy-4-methyl-1-octene-6-inyl]-1H-cyclopenta[b]benzofuran-5-butyric acid. This compound has the following structure.

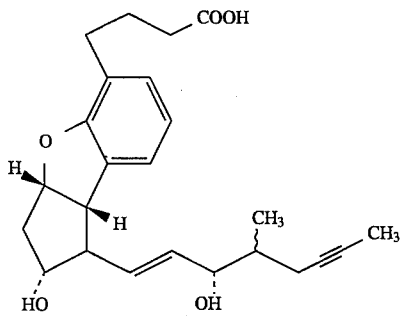

Berlaprost is described in Japanese Laid-open Patent Application (Kokai) Nos. 58-32277, 57-144276 and 58-24778 and the like as a $PGI_2$ derivative having a structure in which the exoenol moiety characteristic to beraprost is converted to inter-m-phenylene structure. However, it is not known that beraprost has an activity to inhibit metastasis of malignant tumors.

The beraprost which is an effective ingredient of the agent of the present invention includes not only racemic body, but also d-body and l-body. Beraprost can be produced by, for example, the method described in the above-mentioned Japanese Laid-open Patent Application (Kokai) No. 58-124778. The salts of beraprost include any pharmaceutically acceptable salts including alkaline metal salts such as sodium salt and potassium salt; alkaline earth metal salts such as magnesium salt and calcium salt; ammonium salt; primary, secondary and tertiary amine salts; and basic amino acid salts.

The term "malignant tumor" used herein includes all tumors such as melanoma, lung cancer, stomach cancer, liver cancer, breast cancer, colon cancer, brain cancer, head and neck cancer and the like. Further, the term also includes cancers of animals such as mouse, human, monkey, dog and the like in which the existence of malignant tumors have been confirmed. Thus, the term "malignant tumor" is not restricted by the organ or species originated therefrom.

To utilize an antimetastasis agent of malignant tumors according to the present invention, beraprost alone or a salt thereof may be used as it is, but it is usually used as orally administerable popular medical formulations together with an adjuvant, for example, with a vehicle, in the form of tablets, capsules, powder, granules, solutions and the like. These formulations can be prepared according to conventional methods. For example, when tablets are prepared, starch, lactose, crystalline cellulose or the like is used as the vehicle. An example of formulation containing 20 μg of beraprost is described in the following examples. These tablets are orally administered usually 3 tablets at a time and 3 times a day per an adult.

The agent according to the present invention exhibits excellent therapeutic effect by oral administration. However, since it has a chemically stable structure and so there is no difficulty in formulation, it can be formulated into a variety of formulations such as injection solutions, suppositories and the like. In case of oral administration, the dose is usually 1–500 μg/day, preferably 10–200 μg/day (based on the weight of the effective ingredient) per an adult.

EXAMPLES

The invention will now be described by way of examples thereof. It should be noted that the examples are presented for the illustration purpose only and should not be interpreted in any restrictive way.

EXAMPLE 1

[Effectiveness on Blood-mediated Metastasis in Mice of Mouse Melanoma B16F10]

Liquid-cultured mouse melanoma cells were transplanted in tail veins of C57/BL6 mice (6 weeks old, male) in an amount of $10^6$ cells/mouse. Simultaneously, beraprost sodium salt was administered intravenously at a dose of 0.03 mg/kg, 0.1 mg/kg or 0.3 mg/kg. To a control group, phosphate buffer saline was administered. Fourteen days after the administration, mice were sacrificed and the lung was removed from each mouse. From the trachea communicating to the lung, 10% neutral buffered formalin solution was poured to inflate the lung, and the lung was immersed in 10% neutral buffered formalin solution to fix the lung. Several days later, each lung was divided and the number of the metastasized nodes on the surface of each leaf was counted with a stereoscopic microscope.

As shown in Table 1, beraprost inhibited the metastasis of B16F10 to mouse lungs at a maximum inhibition rate of 52%. From these results, it was clearly observed that beraprost has a strong activity to inhibit metastasis of malignant tumors.

The statistical analysis of this example was carried out according to the student's t-test.

TABLE 1

| | Dose (mg/kg) | Number of Metastasized Nodes (mean ± standard error) | Metastasis Inhibition Rate (%) |
|---|---|---|---|
| Control Group | | 331 ± 16 | |
| Beraprost | 0.03 | 204 ± 24 | 48*** |
| | 0.1 | 160 ± 28 | 52*** |
| | 0.3 | 167 ± 21 | 49*** |

***: $p < 0.001$

EXAMPLE 2

[Acute Toxicity Test]

Acute toxicity test was carried out using rats. $LD_{50}$ values of the compound for each administration route and sex are shown in Table 2.

As for the pathological observation, the main findings which were common to male and female and to all of the administration routes were, in the cases wherein the mice were killed, slight to medium congestion in lung, slight to medium bleeding in glandular stomach and slight small intestine catarrh.

Thus, it was clarified that side effects are observed only at very high dose.

TABLE 2

| Administration Route | Observation Period (Days) | Sex | Number of Animals | $LD_{50}$* (mg/kg) |
|---|---|---|---|---|
| Oral | 14 | Male | 10 | 15 (13–19) |
| Oral | 14 | Female | 10 | 12 ( 9–15) |
| Intravenous | 14 | Male | 10 | 18 (15–22) |
| Intravenous | 14 | Female | 10 | 13 (10–16) |
| Subcutaneous | 14 | Male | 10 | 13 (12–14) |
| Subcutaneous | 14 | Female | 10 | 7 ( 6–9) |

*Litchfield-Wilcoxon Method (see J. Pharmacol. Expl. Therap. Vol. 96, p. 99 (1949)
The numbers in parentheses indicate 95% reliable limit.

EXAMPLE 3

Tablets according to the present invention were prepared according to the prescription shown in Table 3.

TABLE 3

| | Component | mg/tablet |
|---|---|---|
| Crude Tablets | Beraprost | 0.02 |
| | Lactose | 64.98 |
| | Corn Starch | 25.00 |
| | Crystalline Cellulose | 7.50 |
| | Hydroxypropylcellulose | 2.20 |
| | Magnesium Stearate | 0.30 |
| | Subtotal | 100.00 |
| Film | Hydroxypropylmethylcellulose 2910 (JP) | 4.70 |
| | Macrogolum 6000 (JP) | 0.30 |
| | Carnauba wax | Small Amount |

TABLE 3-continued

| Component | mg/tablet |
|---|---|
| Subtotal | 5.00 |
| Total | 105.00 |

INDUSTRIAL APPLICABILITY

The antimetastasis agent of malignant tumors according to the present invention prominently inhibits the metastasis of malignant tumors and is safe. Further, it is chemically stable. Therefore, it can be used for inhibiting metastasis of malignant tumors in the bodies of patients suffering from malignant tumors by systemic administration.

We claim:
1. A method inhibiting a metastasis of a malignant tumor in a patient, the method comprising:
   administering to said patient an effective metastasis inhibiting amount of beraprost, or a stereoisomer thereof;
   provided that said patient is selected from the group consisting of a human, a monkey, a dog and a mouse, and that said patient is suffering from said malignant tumor; and
   provided that said malignant tumor is selected from the group consisting of a melanoma, lung cancer, stomach cancer, liver cancer, breast cancer, colon cancer, brain cancer, a neck cancer and a head cancer.
2. A method for inhibiting metastasis of a malignant tumor comprising administering an effective amount of beraprost to a patient suffering from the malignant tumor.

* * * * *